(12) United States Patent
Brockoff et al.

(10) Patent No.: US 6,517,732 B1
(45) Date of Patent: Feb. 11, 2003

(54) METHOD OF REMOVAL OF AIR FROM BLOOD

(75) Inventors: Alexander Brockoff, Schaan (LI); Hans Plechinger, Cranbrook (CA)

(73) Assignee: Convergenza AG, Vaduz (LI)

( * ) Notice: Subject to any disclaimer, the term of this patent is extended or adjusted under 35 U.S.C. 154(b) by 0 days.

(21) Appl. No.: 09/638,126

(22) Filed: Aug. 14, 2000

Related U.S. Application Data

(63) Continuation-in-part of application No. 08/998,500, filed on Dec. 26, 1997, now abandoned, which is a continuation of application No. 08/571,490, filed on Dec. 13, 1995, now Pat. No. 5,824,212.

(51) Int. Cl.[7] .............................. B01D 19/00; B04C 3/00
(52) U.S. Cl. ...................... 210/782; 210/787; 210/788; 604/5.01; 95/156; 95/216; 95/261; 95/271; 55/459.1
(58) Field of Search .................................. 210/781, 782, 210/787, 788, 188, 512.11; 55/459.1; 95/156, 216, 241, 261, 271; 96/155, 204; 604/4.01, 5.01, 6.01

(56) References Cited

FOREIGN PATENT DOCUMENTS

GB        2 063 108 A    *    6/1981

* cited by examiner

Primary Examiner—David A. Reifsnyder
(74) Attorney, Agent, or Firm—Beck & Tysver, P.L.L.C.

(57) ABSTRACT

A method and apparatus for removing air from blood which contains air. The air-containing blood is conducted through a cyclone device as a rotating cyclone stream, so that centrifugal forces for the separation of the air from the blood are produced in the rotating cyclone stream.

10 Claims, 5 Drawing Sheets

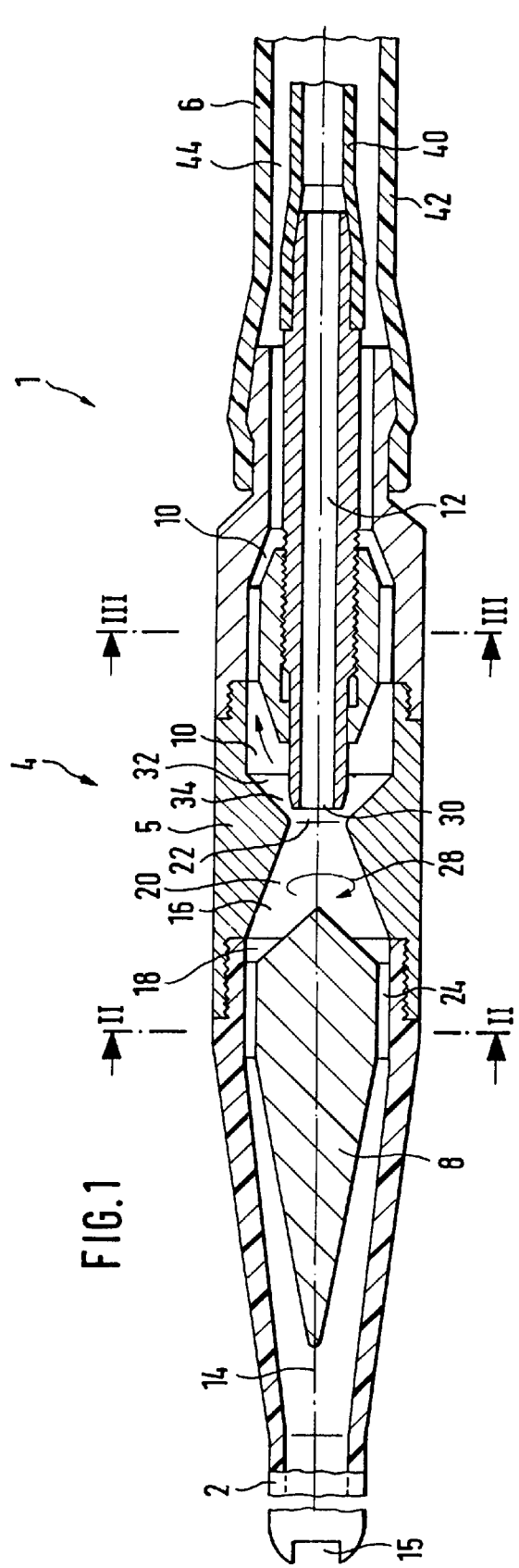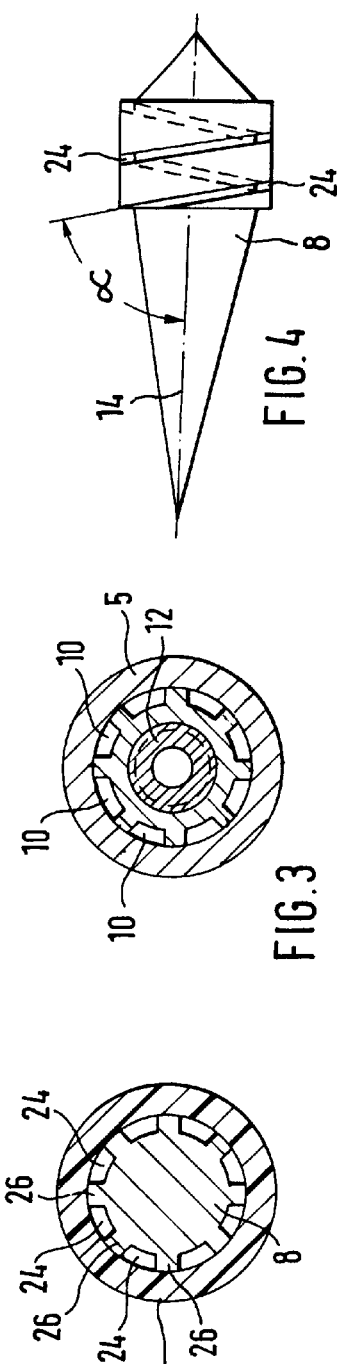

METHOD OF REMOVAL OF AIR FROM BLOOD

CROSS REFERENCE

This Application is a Continuation-in-Part of U.S. patent application Ser. No. 08/998,500, filed Dec. 26, 1997, now abandoned, which is a continuation of U.S. patent application Ser. No. 08/571,490, filed Dec. 13, 1995, which issued as U.S. Pat. No. 5,824,212, which in turn is related to German Application 195.45.404.9 filed Dec. 6, 1995.

The present invention relates to a process and an apparatus for removing air from air-conditioning blood in accordance with the independent claims.

The invention relates, in particular, to the removal of air from a flowing stream of blood which is drawn off from a patient, for instance from a wound or place of operation, or from a blood-container of a blood-donor device.

Upon the drawing off of blood, for instance from a patient during an operation, air is frequently also drawn in from the environment. The air mixes with the blood and leads to damage to the components of the blood. In this way, treatment and reuse of the blood is made difficult.

In actual practice today, blood is drawn off from the operating wound of a patient by systems which consist of a cannula, a conveyor system in the form of a roller pump or a vacuum pump, a blood recirculation system, and connecting lines. These known systems extensively traumatize (damage) the blood.

The reasons for the traumatizing of the blood by the known systems are, among others, the following:
1. The active drawing off of blood from the operating region of a patient results in an intense mixing of the liquid phase (blood) with the gaseous phase (air). This mixing takes place not only at and in the suction cannula but also in the connecting lines, and it constitutes the main factor for the traumatizing of the blood.
2. In order to achieve an effective drawing-off of the blood, the known systems require a relatively high vacuum, which causes additional damage to the components of the blood.

More recent systems for the drawing off of blood are therefore developed in such a manner that they can separate the gaseous phase from the liquid phase so as to limit the damage done to the blood. The known systems are, however, bulky, large, heavy, difficult to operate, and expensive to manufacture. One such system is known, for instance, from U.S. Pat. No. 4,388,922.

The object of the invention is to create a blood-air separation system which has a less traumatic effect on blood and with which even micro-small air bubbles can be removed from a flowing stream of blood.

The invention is of particular advantage in operations with heart-lung machines, liver transplants, many other operations in body cavities and, in general, in the case of blood donations with a blood oxygenator.

Furthermore, the system in accordance with the invention is to be so developed that air present in the blood drawn off can be removed from the blood shortly behind the place where the blood is drawn off, and in particular close to the patient. The system is to be of low cost and easy to use. The system of the invention is to make the following possible:
1. Maximum separation of the gaseous phase (air), even if it consists of small air bubbles of a diameter of only a few $\mu$m, from the liquid phase (blood), preferably immediately and directly at or close to the place where the blood is drawn off;
2. A reduction in the vacuum necessary for the drawing off. This object is achieved in accordance with the invention by the independent claims.

In accordance with the invention, the blood is placed in an eddying in a cyclone, so that the heavy components of the blood-air mixture are forced radially outward by centrifugal force while the physically lighter components and thus, in particular, the air are forced into the radial center of the cyclone eddy stream. By separate drawing off of the radially outwardly forced liquid phase and of the gaseous phase forming radially within it, the gaseous phase is separated from the liquid phase.

In the present specification and the drawings, only embodiments with one cyclone are shown. However, it is clear to the person skilled in the art that several cyclones in parallel or in series can also be used. The following description of a cyclone is therefore representative of embodiments having several cyclones used in parallel or in series.

In one preferred embodiment of the invention, the cyclone is arranged in a small handle part of a blood-suction cannula. This has the advantage that the air is separated from the blood directly behind the place of removal of the blood and that the cyclone is in a position which is favorable from a standpoint of weight. The cyclone can be integrated into the blood-suction cannula or be arranged at the downstream end of the blood-suction cannula. The outer wall of the cannula and/or of the handle part preferably at the same time forms the outer wall of the cyclone.

Further features of the invention are set forth in the dependent claims.

The invention will be described below with reference to the drawings on the basis of several preferred embodiments as examples. In the drawings:

FIG. 1 is an axial longitudinal section through a blood-suction device in accordance with the invention, on a scale of 4:1;

FIG. 2 is a cross section along the plane II—II of FIG. 1;

FIG. 3 is a cross section along the plant II—II of FIG. 1;

FIG. 4 is a side view of a body of the blood-suction device of FIG. 1;

Figure 5:
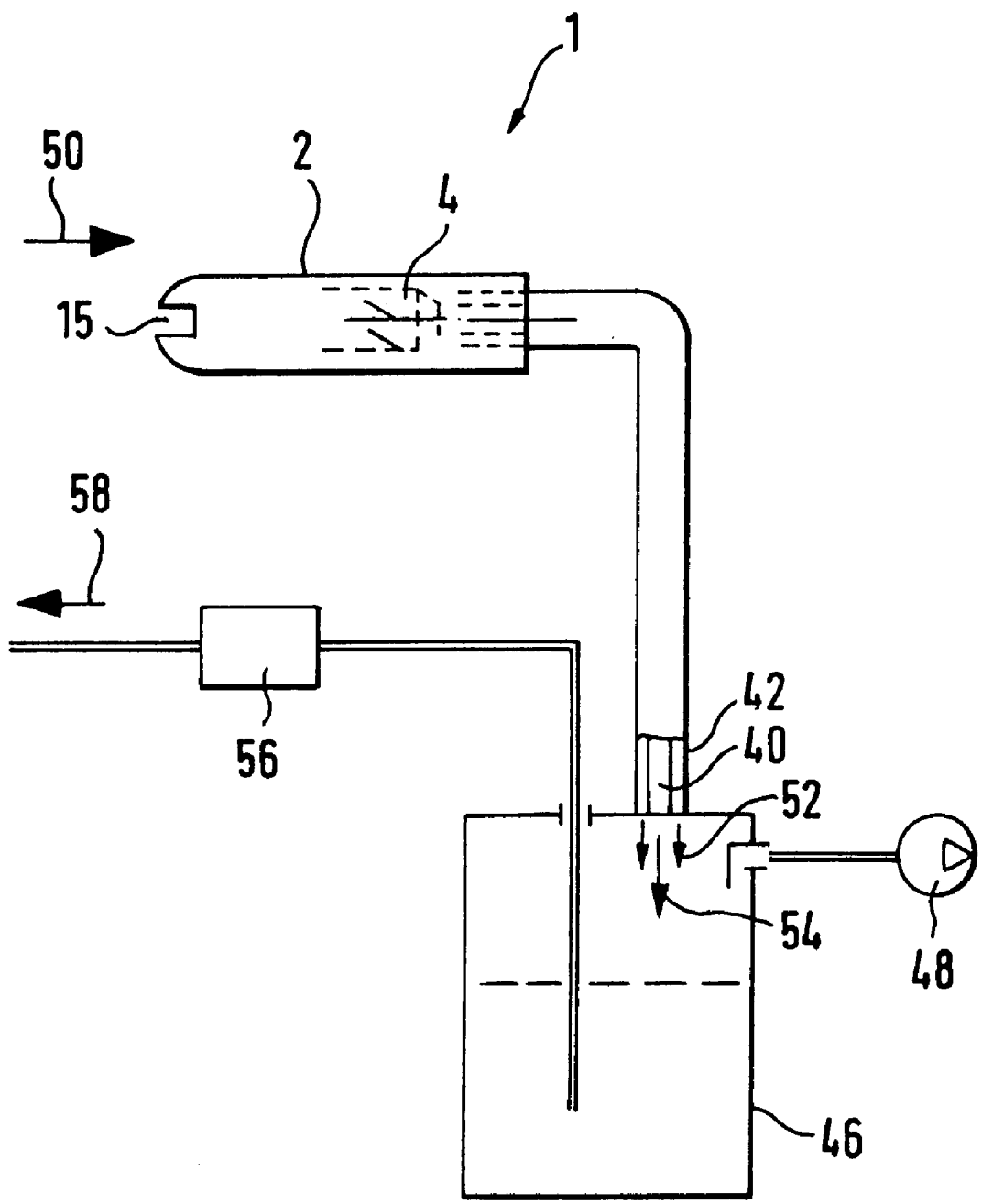
FIG. 5 shows diagrammatically the use of a blood-suction device in accordance with FIG. 1 in a system for the drawing off of blood from a patient, treatment of the blood and recirculation of the blood back to the patient.

The blood-suction device 1 of FIGS. 1 to 4 consists of a blood-suction cannula 2, a cyclone device 4 on the downstream end of the blood-suction cannula 2, and a double hose or double lumen 6 on the downstream end of the cyclone device 4. The cyclone device 4 contains, within an outer wall 5, a flow guide body 8, a liquid channel 10 of annular cross section, and a gas channel 12 arranged axially in the radial center therein. All parts are arranged axially to a center axis 14. The cyclone wall 5 forms a handle for the blood-suction cannula 2 and can consist of one piece with the blood-suction cannula or, as shown in the drawings, of several parts which can be connected detachably to each other. The blood-suction cannula 2 has a suction inlet 15 on its upstream end. The wall 5 forms a cyclone eddy chamber 16 which consists of an upstream cylindrical section 18 and an adjoining nozzle section 20 which narrows in funnel shape in the direction of flow and has a nozzle opening 22 in the radial center. Helical grooves 24 between helical ribs 26 of the flow-guide body 8 and the cyclone wall 5 resting against them form an "approximately tangential" cyclone inlet on the upstream starting end of the cyclone eddy chamber 16. The expression "approximately tangential" means here a direction which extends precisely in tangential direction 90° to the middle axis 14 or at least so obliquely to the center axis 14 that the axial blood-air-mixture suction stream of the blood-suction cannula 2 in the cyclone eddy chamber 16 flows as eddy stream 28 in circumferential direction along the cyclone wall 5, thereby producing centrifugal forces which drive the blood components (liquid phase) of the mixture suction stream radially outward to the wall 5 and thereby separate them from the radially inwardly displaced air (gaseous phase) of the mixture suction stream. The nozzle section 20 which narrows down in funnel shape produces a reduction in the available cross section of flow and thus in an increase in the velocity of flow of the suction stream in circumferential direction.

The gas inlet 30 of the gas channel 12 forms the gas outlet of the cyclone eddy chamber 16 and has a smaller cross section than the nozzle opening 22 and is located only a short distance away, downstream from said nozzle opening 22. The liquid inlet 32 of the liquid channel 10 forms the blood outlet of the cyclone eddy chamber 16 and is formed in ring-shape between the gas inlet 30 of the gas channel 12 and a diffusor channel section 34 which widens in cross section in funnel shape in the direction of flow and follows behind the nozzle opening 22. The gas channel 12 and its gas inlet 30 consist of a tube which is replaceably inserted into the cyclone wall 5. The cyclone nozzle section 20 which narrows down in funnel shape results in an acceleration of the flow and the diffusor channel 31 which widens in funnel shape and follows it effects a slowing down of the cyclone eddy stream. By this combination, better efficiency is obtained in the separation of air and blood.

Figure 6:
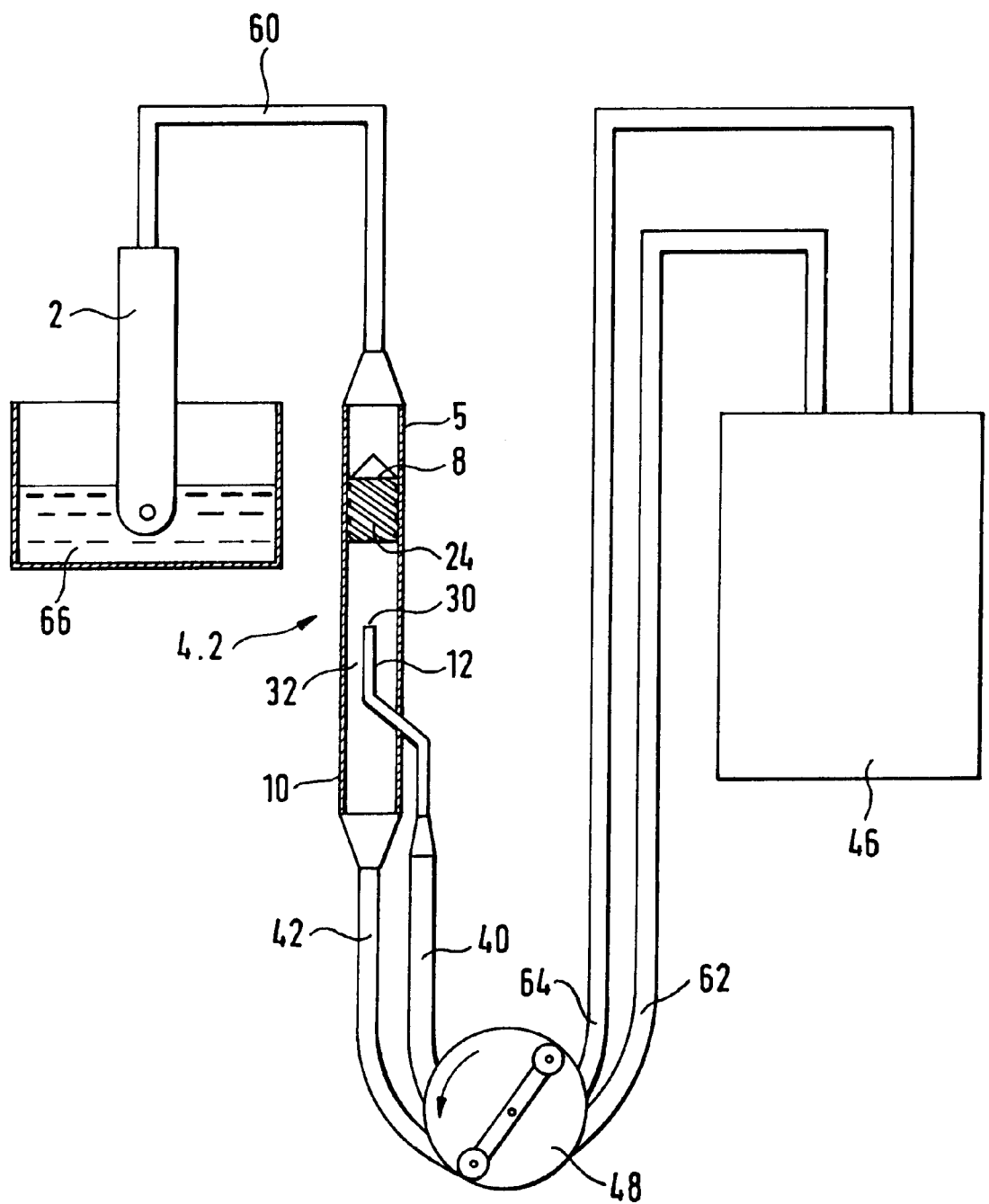
FIG. 6 shows diagrammatically another embodiment of the blood-suction device in accordance with the invention.

The double hose 6 consists of a radially inner hose 40 which is connected to the downstream end of the tube of the gas channel 12 and of a radially outer tube 42 which surrounds the inner hose 40 spaced radially from it and is connected to the downstream end of the cyclone wall 5 in such a manner that the liquid channel 10 is in flow communication with the space 44 which is formed between the two tubes 40 and 42. The two tubes 40 and 42 are connected at their downstream ends (not shown) to a source of suction 48 either directly, as shown in FIG. 6, or with the interpositioning of the blood reservoir 46, as shown in FIG. 5. The grooves 24 in the flow guide body can have a varying angle of slop alpha of from approximately zero degrees on the upstream starting end to about ninety degrees at the downstream end, with reference to the middle axis 14 in accordance with FIG. 4.

FIG. 5 diagrammatically shows the blood-suction device 1 which draws blood and air in the direction of an arrow 50 from a wound, for instance an operating wound, through the suction inlet 15 of the blood-suction cannula 2, separates the blood-air-mixture suction stream in the cyclone device 4 into a blood phase 52 and a gaseous phase 54 and draws both phases 52 and 54 into the blood reservoir 46. The suction source 48 is connected to the blood reservoir 46 above its liquid level. The blood can be recirculated from the blood reservoir 46 via a blood-treatment and blood-conveying device 56 in the direction indicated by an arrow 58 back into the circulation of the patient or be introduced into blood banks.

In the embodiment shown in FIG. 6, the source of suction 48 is a roller pump which is arranged in the path of flow between another embodiment of a cyclone device 4.2 and the blood reservoir 46. The blood-suction cannula 2 can be connected in an arc or via a short connecting tube 60 to the upstream end of the cyclone device 4.2. The downstream end of the cyclone device 4.2 is connected by the two tubes 40 and 42 to the suction side of the roller pump 48. The delivery side of the roller pump 48 is connected via a tube 62 for the liquid phase (blood) and a separate tube 64 for the gaseous phase (air) to the blood reservoir 46. The patient 66 is indicated merely diagrammatically in the form of a blood vessel.

Figure 7:
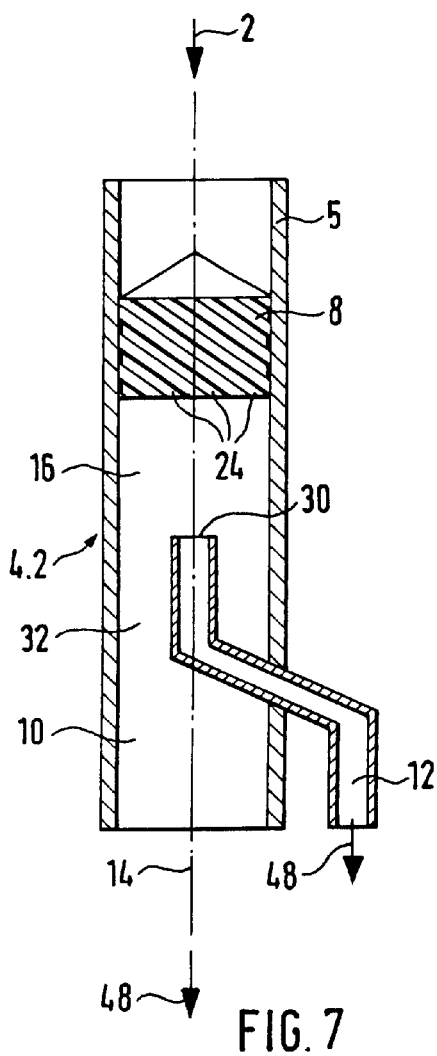
FIG. 7 is a diagrammatic axial section through another embodiment of a cyclone in accordance with the invention, similar to FIG. 1.

The cyclone device 4.2 of FIG. 6 which is shown in FIG. 7 contains a flow body 8 the upstream end of which has the shape of a cone of short cone height and the downstream end of which is flat. The cyclone eddy chamber 16 is of a circular cylindrical shape over its entire axial length. The gas inlet 30 of the gas channel 12 is arranged in the radial center of the eddy stream 28 produced by the flow guide body 8. The gas channel 12 is extended laterally out of the cyclone eddy chamber 16 downstream of its inlet 30 so that, in this embodiment, the two hoses 40 and 42 are not coaxial to each other but lie outside of one another.

In the embodiments described above, the middle axis 14 extends horizontally, vertically or obliquely in the cyclone device 4 or 4.2 depending on the position of the operator.

Figure 8:
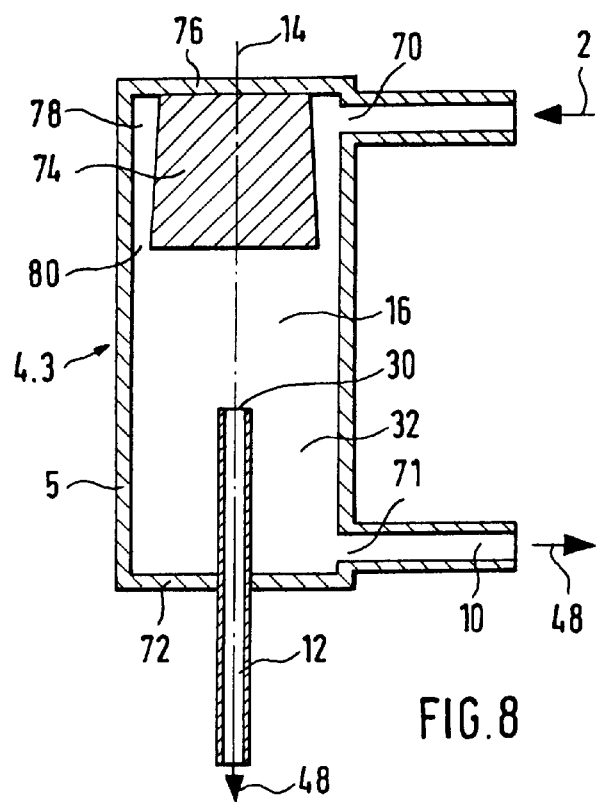
FIG. 8 shows a diagrammatically an axial section through another embodiment of a cyclone in accordance with the invention.
Figure 9:
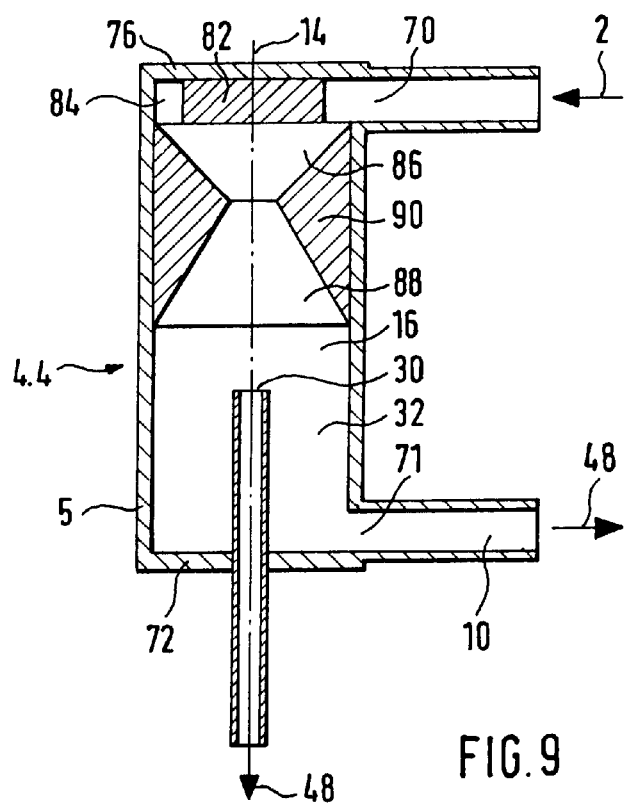
FIG. 9 shows diagrammatically an axial section through another embodiment of a cyclone for the separating of air from a flowing stream of blood in accordance with the invention.

The embodiments of cyclone devices 4.3 and 4.4 shown in FIGS. 8 and 9 can be placed as independent units on a base so that the middle axis 14 of the cyclone devices 4.3 and 4.4 is vertical. Each of the cyclone devices 4.3 of FIG. 8 and 4.4 of FIG. 9 has a circular cylindrical cyclone wall 5; on the upper, upstream end of the wall 5 a tangential cyclone inlet 70 which is connected to a blood-suction cannula 2, not shown; at the lower, downstream end of the wall 5, a tangential first cyclone outlet 71 which is a part of the liquid channel 10 the inlet 32 of which is formed by the annular space between the cyclone wall 5 and the gas channel 10; a second cyclone outlet in the form of the inlet 30 of the gas channel 12 which extends through an eddy-chamber bottom 72 so that the inlet 30 of the gas channel 12 is arranged in the radial cyclone center of the eddy chamber 16 upstream of the liquid inlet 32 of the liquid channel.

In the embodiment shown in FIG. 8, there is present in the cyclone eddy chamber 16 a conical insert body 74 which extends from an eddy-chamber cover 76 above the cyclone inlet 70 past the cyclone inlet 70 and forms, between itself and the cyclone wall 5, an annular nozzle channel 78 concentric to the middle axis 40 which narrows in wedge shape from the cyclone inlet 70 an annular nozzle opening 80 and thereby accelerates the blood-air-mixture suction stream. The downstream side of the insert body 74 is flat at a right angle to the middle axis 14 and is spaced from the inlet 30 of the gas channel 12.

The cyclone device 4.4 of FIG. 9 is provided on the inner side of its eddy-chamber cover 76 with a circular-cylindrical insert body 82. The insert body 82, together with the cyclone wall 5, forms an annular chamber 84 in the region of the cyclone inlet 70. The annular chamber 84 is followed, in direction of flow, along the middle axis 14 by a nozzle section 86 which narrows down in funnel-like manner and then by a diffusor section 88 which widens in funnel shape and is located with axial spacing axially opposite the inlet 30 to the gas channel 12. The nozzle section 86 and the diffusor section 88 are formed by a second insert body 90 which is inserted into the cyclone wall 5.

The cyclone devices of the invention form a "dynamic air separator" since it is traversed by the blood and in this connection removes air from the blood. The cyclone devices still have a good air-separation efficiency even in the case of very small amounts of blood and very small air bubbles of a size of only a few $\mu$m.

Figure 10:
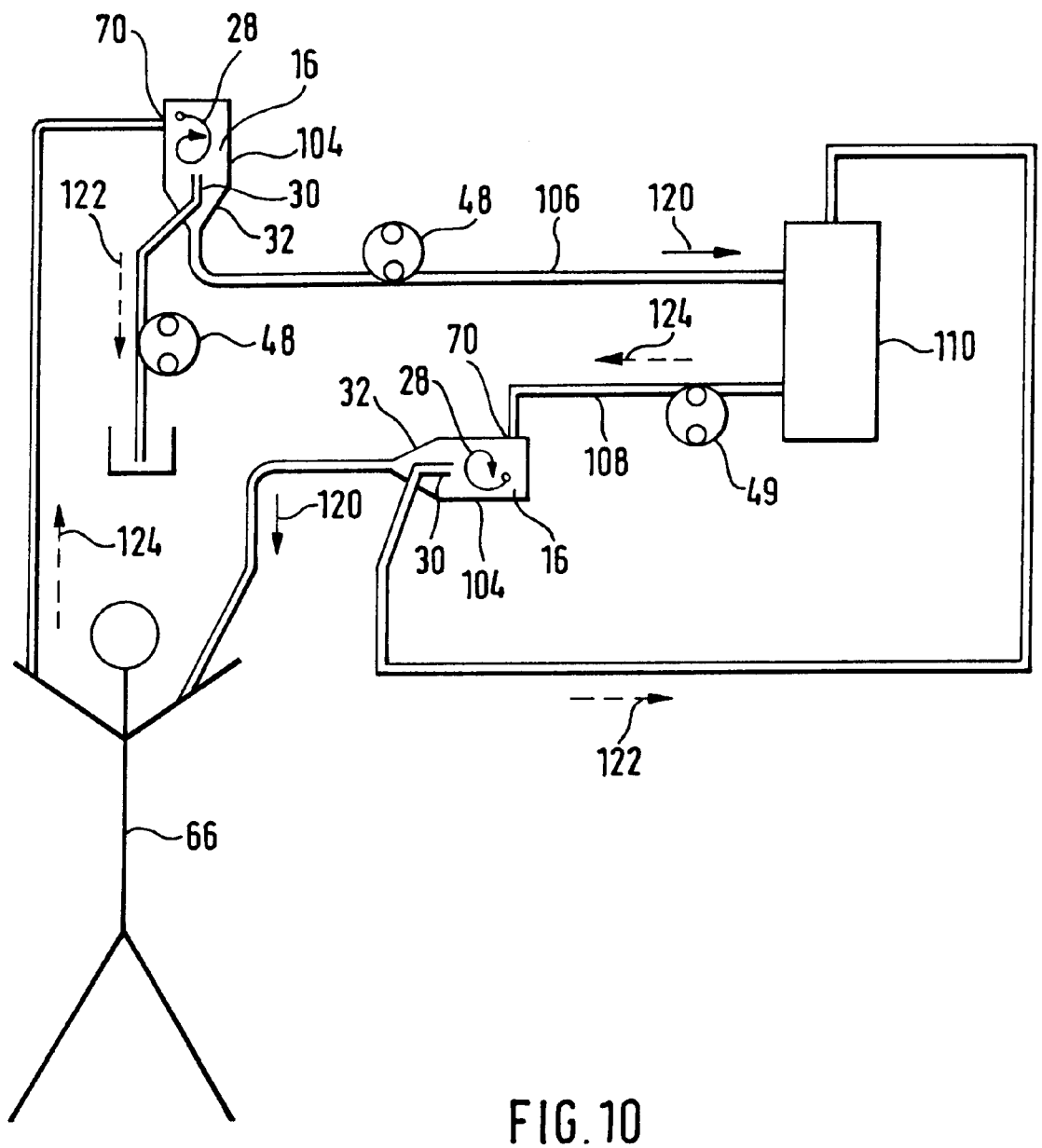
FIG. 10 shows diagrammatically a device in accordance with the invention for the separating of air from a flowing stream of blood both in forward passage and in return passage between a patient and a blood-treatment device, for instance a heart-lung machine, which has an oxygenator for the enriching of oxygen in the blood.

The device in accordance with the invention which is shown in FIG. 10 contains a cyclone 104 in the forward travel path 106 and a cyclone 104 in the return travel path 108 of a blood circulation from a patient 66 to a heart-lung machine 110 which contains an oxygenator for enriching the oxygen in the blood, and back again to the patient 66. For the drawing off of the blood from the patient 66, there is a pump 48 in the forward path 106 between its cyclone 104 and the heart-lung machine 110. The gaseous phase can be drawn from the cyclone 104 of the forward path 106 by a separate flow path of the same pump or by a second pump 48.

In the return travel 108, there is a pump 49 between the heart-lung machine 110 and its cyclone 104. In this case, the blood is not drawn through this cyclone 104 but driven through it. The gaseous phase of this cyclone 104 in the return path 108 can be returned by the conveying force of the pump 104 into the heart-lung machine 110.

The cyclones 104 of the forward path 106 and the return path 108 have a tangential inlet 70 at one axial end of a circular cyclone eddy chamber and, at their other, axial end, a blood outlet 32 at the cyclone-chamber wall and an air outlet 30 in the radial center of the cyclone eddy chamber 16.

The forward path 106 and the return path 108 form two different processes which can be used separately from each other or, in accordance with FIG. 10, in combination with each other. The cyclone 104 in the forward path 106 serves for the separating of air drawn off, undesired, from the patient from the blood which is drawn off at the same time from the patient. The cyclone 104 in the return path 108 serves for the separating of very small air bubbles of a diameter within the $\mu$m range which pass in the oxygenator of the machine 110 into the blood which is conveyed to the patient.

In accordance with an embodiment which is not shown in the drawing, the pump 48 in the forward path can be omitted and its suction action produced by the pump 48 of the return path 108 through the machine 110. In FIG. 10, the solid line arrows 120 indicate the direction of flow of the blood and the dashed-line arrows 122 the direction of flow of the air, while the combined solid-dashed lines 124 indicate the direction of flow of the blood-air mixture.

The blood-suction place can be a wound, an operating site or any desired blood vessel of a patient 66, or a container, for instance a blood bank, or a machine, for instance a heart-lung machine 100 and/or an oxygenator for the enrichment of the oxygen in the blood.

Turning to FIG. 1 there is shown a version of the device which has a middle axis 14. The inlet port located near items 2,5 in the figure, is located inline with the axis 14 and concentric with it. The outlet port 10 and the micro-bubble take off or extraction port 30 are also concentric with the axis 14. This collection of features may be referred to as an axial flow device because their is a strong axial component of flow to the blood while the micro-bubbles are being extracted by the inventive process. For this discussion micro-bubbles are extremely small bubbles that form is blood during perfusion, These bubble are on the order of a few micrometers in diameter. They are invisible to the naked eye and they cause injury to the patients if introduced to the patient. These bubbles also injure the blood.

The blood enters a substantially circular tube which leads the blood flow to the flow guide body 8. It is important to note that the conical shape of the flow body causes an axial acceleration of the blood as it flows along this surface due to the well know Bernoulli principle. This axial acceleration occurs prior to the blood entering the helical chamber defined by the "screw" shape shown best in FIG. 2. and FIG. 4. The helical grooves 24 and the helical ribs 26 define a helical flow path around the central or middle axis 14. This element is located between the inlet port and the outlet port. Thus in practice the blood is first linearly accelerated along a straight path and then it is accelerated radially in the helix. Depending on the pitch "alpha" of the ribs 26 the blood may undergo additional linear or axial accelerations well as the radial acceleration in the helix.

The blood experiences a pressure gradient within the helix and the micro-bubbles begin to migration this field. The micro-bubble begin to move toward and remain at the center of the flow along the middle axis 14. In this fashion decelerating the blood flow along the central axis prior to the location of said bubble extraction port, permits the micro-bubbles enough time to migrate toward the central axis to increase the concentration of micro-bubbles in blood flow extracted from the bubble extraction port.

After the helical accelerating the blood is delivered to the nozzle section 20 seen best in FIG. 1. the contour of the cylindrical section 18 and the nozzel section togeather cooperate to slow the blood down in the axial direction, this results from the gradually increasing crsosection which both slows the blood and minimizes the rate at which pressure changes in the device. This process permits the blood to continue to spin around the axis 14. retaining the micro-bubble confined to the central axis 14. This deceleration of the blood flow along the central axis prior to the locaiton of the bubble extraction port allows the micro-bubbles enough time to collect along the center line or axis 14.

The bubble extraction port 12 in the figure forms a "gas channel" where the micro bubbles are removed. In practice a small amount of blood carries the enriched concentration of microbubbles out of the system. The size of the extraction port may vary. In general the large the opening the greater the number of microbubble removed. However, large apertures carry off a substantial amount of blood. Smaller openings are more efficient in terms of reduced blood loss. Some experimentation must be performed to optimize a device for a particular medical application

What is claimed is:

1. A method of removing micro-bubbles from blood, comprising the steps of:

defining an axial flow path in a device having a central axis, an inlet port, an outlet port and bubble extraction port;

defining a helical flow path around said central axis positioned between said inlet port and said outlet port; said defining step performed by a spiral helical rib wound symmetrically around said central axis and placed concentric with said central axis;

introducing blood into said inlet port;

accelerating blood containing micro-bubbles from said inlet port, along said helical path, whereby said blood experiences a pressure gradient sufficient to force said micro-bubbles to migrate toward said central axis;

positioning said bubble extraction port proximate said central axis, whereby said micro-bubbles are extracted with blood flow from said bubble extraction port.

2. The method of claim 1 further comprising:

accelerating said blood along said central axis prior to accelerating said blood in said helical flow path.

3. The method of claim 1 further comprising:

decelerating said blood flow along said central axis prior to the location of said bubble extraction port.

4. The method of claim 1 further comprising:

accelerating said blood along said central axis prior to accelerating said blood in said helical flow path; and decelerating said blood flow along said central axis prior to the location of said bubble extraction port, whereby said micro-bubbles are given enough time to migrate toward said central axis to increase the concentration of micro-bubbles in blood flow extracted from said bubble extraction port.

5. The method of claim 1 wherein said helical path definition step is performed by:

intercepting blood flow in a helical chamber formed by a helical rib symmetrically aligned around said aligned along said central axis.

6. The method of claim 5 wherein said helical path definition step is performed by:

intercepting blood flow in a helical chamber having a constant cross section as measured along said flow path and wherein said chamber is aligned geometrically along said central axis.

7. The method of claim 1 wherein said inlet port is concentric with said central axis.

8. The method of claim 1 wherein said outlet port is concentric with said central axis, has a single aperture exposed to the bubbles and is symmetrical in cross section and aligned along said central axis.

9. The method of claim 1 wherein said bubble extraction port is concentric with said central axis.

10. A method of removing micro-bubbles from blood, comprising the steps of:

defining an axial flow path in a device having a central axis, an inlet port, an outlet port and bubble extraction port, each port being concentric with said central axis and each port being substantially annular and circular in cross section;

defining a helical flow path around said central axis with a spiral helical rib symmetrically placed around said central axis, said helical flow path positioned between said inlet port and said outlet port, said helical flow path having a constant cross section as measure perpendicularly to local flow;

introducing blood into said inlet port;

accelerating blood containing micro-bubbles from said inlet port, along said helical path, whereby said blood experiences a pressure gradient sufficient to force said micro-bubbles to migrate toward said central axis;

positioning said bubbles extraction port proximate said central axis, whereby said micro-bubbles are extracted with blood flow from said bubble extraction port;

extracting blood largely devoid of micro-bubbles from said outlet port.

* * * * *